United States Patent
Hofmann

(10) Patent No.: US 7,279,094 B2
(45) Date of Patent: Oct. 9, 2007

(54) CHROMATOGRAPHY METHODS AND CHROMATOGRAPHY APPARATUS

(75) Inventor: Martin John Hofmann, Stroud (GB)

(73) Assignee: Pall Corporation, East Hills, NY (US)

( * ) Notice: Subject to any disclaimer, the term of this patent is extended or adjusted under 35 U.S.C. 154(b) by 379 days.

(21) Appl. No.: 11/088,567

(22) Filed: Mar. 24, 2005

(65) Prior Publication Data

US 2005/0167364 A1    Aug. 4, 2005

Related U.S. Application Data

(62) Division of application No. 10/089,493, filed as application No. PCT/GB01/03403 on Jul. 30, 2001, now Pat. No. 6,966,991.

(30) Foreign Application Priority Data

Jul. 28, 2000    (GB) ................ 0018522.3
May 14, 2001    (GB) ................ 0111785.2

(51) Int. Cl.
*B01D 15/08*    (2006.01)

(52) U.S. Cl. ............... 210/198.2; 210/635; 210/656; 422/70

(58) Field of Classification Search ............... 210/635, 210/656, 198.2, 96.1; 141/12, 80; 422/70; 436/161
See application file for complete search history.

(56) References Cited

U.S. PATENT DOCUMENTS

| | | | |
|---|---|---|---|
| 4,175,037 A | 11/1979 | Benney et al. |
| 4,324,131 A | 4/1982 | Rosencwaig |
| 4,919,804 A | 4/1990 | Dorsey et al. |
| 5,061,371 A | 10/1991 | Tabata et al. |
| 5,453,163 A | 9/1995 | Yan |
| 5,597,962 A | 1/1997 | Hastings et al. |
| 5,610,322 A | 3/1997 | Unger et al. |
| 6,446,679 B2 | 9/2002 | Hofmann et al. |

FOREIGN PATENT DOCUMENTS

| | | |
|---|---|---|
| EP | 1 096 253 A2 | 5/2001 |
| GB | 1312096 | 4/1973 |
| GB | 2258415 A | 2/1993 |
| WO | WO96/10451 A1 | 4/1996 |
| WO | WO99/64130 A1 | 12/1999 |

*Primary Examiner*—Ernest G. Therkorn
(74) *Attorney, Agent, or Firm*—Leydig, Voit & Mayer, Ltd.

(57) ABSTRACT

Ultrasound transceivers (20) are distributed up the side wall of a chromatography column (1) and enable tracking of the progress of a rising bed front (5) during packing. Comparison with a predetermined stored profile is used for feedback control of the packing pump P. Other uses of ultrasound monitoring of the column interior are disclosed.

17 Claims, 17 Drawing Sheets

CHROMATOGRAPHY METHODS AND CHROMATOGRAPHY APPARATUS

This application is a division of application Ser. No. 10/089,493, filed Jul. 16, 2002, now U.S Patent No. 6,966,991, which, in turn, is a 371 of PCT/GB01/03403, filed Jul. 30, 2001.

FIELD OF THE INVENTION

This invention has to do with methods and apparatus used in chromatography. The new proposals are concerned with finding out the condition of a bed of a particulate medium in the bed space of a chromatography column. This assessment might be during the packing of the column or afterwards i.e. during or after a chromatography process using the packed bed.

BACKGROUND OF THE INVENTION

The conventional principles and apparatus for packed-bed chromatography are well-established. The present invention is concerned with issues arising in commercial-scale preparative chromatography, where columns are often very large and any one or more of the particulate packing medium, the product to be separated and the time taken up in arranging the running of the procedure is/are of very high value.

It is well known that a packed column has to be continuously, uniformly and entirely filled with the relevant medium under an appropriate degree of compression of its particles.

Conventional column packing, an operation requiring great care and experience, involves removing the top plate or "cell" of the column and pouring in a slurry of the relevant medium in a liquid carrier. More recently the use of a packing port has become favoured because it obviates taking the lid off. Various kind of valved ports have been proposed for this; see for example GB-A-2258415, WO 96/10451 and WO 99/64130. The column generally has upper and lower restricted-permeability elements—mesh or sinter layers—to retain the media particles, and the packing port provides communication directly into the bed space past i.e. penetrating one or both of these restricted-permeability layers. To pack, typically the column is filled with liquid and the medium slurry pumped in through the packing port at one end, liquid carrier leaving the column via the permeable element at the other. The particulate medium is retained and gradually accumulates until the column is full. The accumulating bed is compressed by the controlled pressure from the pumped liquid and—in the usual case when packing from the top—also by the weight of the upper part of the bed. There is a subtle, continuous variation in the conditions experienced by the medium. A common procedure is for the operator to continue pumping until the column is essentially full, whereupon the pump usually cuts out spontaneously. As the liquid flow pressure is relieved, the packed bed then "relaxes" to fill the column with a more uniform compression profile over its length.

Even with packing ports, the packing of chromatography columns is a skilled job requiring training and experience. A packing nozzle helps to achieve consistent results, but only experience and time-consuming testing of trial packs can indicate the optimal slurry concentrations and pump pressure profiles for a given medium in a given column. Since many columns are of steel the operator can have very little idea of what is happening inside.

SUMMARY OF THE INVENTION

We have found that by transmitting periodic mechanical vibratory signals, in particular sonic or ultrasonic signals, through the bed space of a column, one can obtain useful information about the condition and/or position of a bed of particulate medium in that space by detecting the transmitted signal. We have confirmed that apparatus to implement these findings is practical to make and use, and that useful results are obtained.

One aspect of the invention is to use the detection of a sonic or ultrasonic transmission through the bed space as a means of improving the process of packing the column, by marking the passage of the advancing "front" of the accumulating bed and/or to observe conditions in the body of the bed which may be of practical importance.

Other aspects relate to detecting the properties of sonic/ultrasonic transmissions through the bed space as a means of noting the presence of other materials in the bed, e.g. components which are eluting through the column, or impurities which may be fixedly bound in the column.

Other aspects are chromatography apparatus adapted for the performance of the various method aspects, comprising one or more sonic/ultrasonic transmitters/detectors.

Further aspects relate to the provision of chromatography packing apparatus enabling a packing procedure to be monitored and to assess its conformity with a predetermined packing profile, and for using automatic or operator-controlled feedback to approximate the actual packing process to the predetermined profile.

Aspects of the invention are set out in the claims.

We have determined that a sonic/ultrasonic transmission through the bed space of a chromatography column is attenuated by the presence of the bed and its speed increased, i.e. its time of flight reduced, compared with when the bed is not present. Either or both of these effects may be used to obtain data about the bed in the column. Also, either or both of these properties (amplitude, speed) can be influenced by the presence of adventitous substances in the bed.

Thus, the present proposals enable any one or more of
  determining a height to which packing medium has accumulated during packing;
  determining a packing density/degree of compression of packed medium;
  determining—by means of plural transmissions along different paths—a rate of advance of the bed front during packing;
  determining the presence/position/extent of contaminant materials or eluting product components in the bed from time to time, e.g. as chromatography proceeds.

Preferably the state of packing of materials within the chromatography column can be assessed by measuring the time taken between transmission and reception of a transmission, i.e. the speed.

Alternatively or additionally, measuring the attenuation of a transmission can be particularly useful in determining the height of a slurry bed within the chromatography column.

Preferably the transmission is directed through the interior of the column in a direction substantially parallel to a base of the column, e.g. in a substantially radial direction so that the transmission crosses through or close to the axis of the column. The transmission may be focussed by a sonic lens.

The transmission is preferably in a pulsed form. This aids detection.

The frequency of the transmission is selected to obtain a suitable detectable signal for the purpose in hand. Preferred frequencies are ultrasonic, e.g. ≧0.5 MHz, ≧1.0 MHz, ≧1.5 MHz. For example a transmission of 2 MHz was found to give a suitable detectable signal. The attenuation suffered by a 2.5 MHz transmission passing through a slurry bed was found to be greater than that at 2 MHz.

When measuring the speed of a transmission minimum attenuation may be desired. When determining the height of a slurry bed within the chromatography column it may be desirable to use a sonic transmission which is more significantly attenuated by passing through the slurry bed.

A sonic/ultrasonic transmitter is used to generate the transmission. The transmitter may be attached to a side wall of the chromatography column, preferably on the outside.

The transmitter may be a transceiver which is capable of detecting as well as transmitting sonic transmissions. Preferably the sonic transceiver comprises a piezoelectric material. Preferably the sonic transceiver is used to transmit a sonic transmission and to receive an echo of this transmission. This technology is known per se e.g. for measuring fluid velocities in pipes.

The time delay of the echo together with the dimensions of the column can be analysed to find the speed of the sonic transmission and thus obtain information about the packing state of the materials therein. The thickness and material of the chromatography column walls can be taken into account as necessary.

Alternatively sonic transmission may be generated by a transmitter and received separately by a receiver. The transmitter and receiver are then preferably on opposite sides of the column.

In the following proposals it is generally possible to use either a sonic transceiver or separate transmitter and receiver.

Preferably the transmitter is attached to the exterior of the side wall of the column. A lens may be placed between the transmitter and the column surface.

Alternatively a transmitter and/or sonic lens may be embedded within the side wall of the chromatography column or even placed within the column.

The transmitter may be placed at any appropriate height. To detect when the slurry bed has reached a given height in the column then one may place a transmitter at this height and to direct the transmission substantially parallel to the base of the column.

Preferably more than one transmission path is provided, at different parts of the interior of the chromatography column. This enables e.g. spatial profile of the packing state of materials within the column, useful in checking the uniformity of packing.

For example transmission paths may be at different axial heights.

Each transmission path may have a respective transmitter/detector pair, or a single sonic transmitter/detector may change its position e.g. by sliding to different positions on the exterior of the column's side wall.

A further aspect of the present invention is a method of packing a chromatography column involving pumping a slurry of particles into the column, using a sonic transmission to monitor the height of said slurry within the column and stopping the pumping when the desired height of said slurry within the column is monitored.

Preferably the stopping of the pumping is automated. Preferably a switching device takes an input based on the amplitude of the monitored sonic transmission and switches off the pump when said input indicates that the desired height of slurry within the column has been reached.

A further aspect is a method of packing a chromatography column involving using a pump to pump a slurry of particles into the column, using a sonic transmission to monitor the state of packing of said slurry within the column, comparing the state of packing monitored to a desired state of packing and when the monitored state of packing is different from said desired state of packing adjusting the packing parameters so as to achieve the desired state of packing.

This aspect of the invention may be used in combination with the aspects above.

The packing parameters are any adjustable parameters which affect the packing process, for example the pumping pressure (which may be adjusted by altering the pumping speed). It may also be possible to adjust the concentration of slurry being pumped into the chromatography column.

Preferably the packing parameters are adjusted by means of feedback to the packing apparatus (e.g. the pump), said feedback being based upon the desired state of packing and the state of packing monitored by the sonic transmission.

Preferably the feedback is automated by the use of a computer or appropriate electronic circuits, but it may be possible for the method to be implemented manually. The feedback may be automated by use of a I to P converter which converts an electric current to a desired pumping pressure. The feedback may be proportional to the difference between the desired state of packing and the state of packing monitored.

Preferably the comparison between the state of packing monitored and the desired state of packing is achieved by comparing the measured speed of the sonic transmission with a desired value for this speed.

Preferably this comparison is carried out continuously during the packing process and continuous feedback to the packing apparatus is generated on the basis of this comparison.

The feedback may enable an increase or decrease in the pumping pressure. For example if the speed of the sonic transmission is lower than the desired value then the density of the slurry is too low and the pumping pressure will need to be increased so as to increase the packing compression and density of the slurry. Equally if the speed of the sonic transmission is higher than the desired value then the packing compression is too high and the pumping pressure will need to be decreased.

Preferably information relating to the desired state of packing is provided in the form of a packing profile which details the transmission properties at various stages during the packing process. These stages may be various points in time since the packing process started. They may be defined by the duration of time for which the pump has been active, a height in the column which the slurry has reached or a volume of slurry which has been pumped.

The packing profile may for example give a profile of the desired speed of the transmission against a time from the start of the packing process.

It is envisaged that the profile may be derived from measurements carried out during a successful trial packing of a chromatography column.

The profile may give a range of acceptable values, rather than an exact value, for the property e.g. speed of the transmission at each stage during the packing process.

The profiles may differ for different combinations of chromatography column type and slurry type. Therefore it is envisaged that a different packing profile may be provided for each such combination.

The packing profile is also expected to vary according to the path of the transmission in the chromatography column.

Preferably the packing parameters are adjusted on the basis of the packing state monitored by respective ones of plural transmissions and the desired packing state for each respective transmission.

A further aspect of the present invention is a system for packing a chromatography column, the system comprising a pump for pumping particulate slurry into the column, signal generating means for generating a signal to control a sonic/ultrasonic transmitter, receiving means for receiving a signal from a corresponding receiver, analysing means for analysing a signal received by the receiving means and outputting a result based on analysis of said received signal and pump controlling means for controlling said pump on the basis of the output from said analysing means.

Preferably the system has data means for storing or for reading packing profile data. Preferably said packing profile data contains chromatography column dimension data.

Preferably the analysing means is capable of detecting a signal received by the receiving means which corresponds to a signal previously generated by the signal generating means, calculating the time delay between the generation and detection of said signal, analysing said time delay along with chromatography column dimension data and thus computing the speed of a sonic transmission corresponding to said generated and detected signal and generating an output based on said computed speed of said sonic transmission.

Alternatively or additionally the analysing means is capable of detecting a signal received by the receiving means which corresponds to a signal previously generated by the signal generating means and generating an output based on the amplitude of said received signal.

Preferably the packing profile data also contains data relating to the type of slurry with which the chromatography column is to be packed. Preferably the packing profile data contains data relating to the desired output from the analysing means during the packing process. Preferably the packing profile data contains data relating to the desired speed of said sonic transmission corresponding to said generated and detected signal.

Preferably the pump control means is capable of controlling the pump on the on the basis of said packing profile data and said outputted result from said analysing means.

Preferably the pump control means is configured to increase the pumping pressure if the result from the analysing means indicates that the velocity of the sonic transmission is lower than desired and to decrease the pumping pressure if the result from the analysing means indicates that the speed of the sonic transmission higher than desired.

It is envisaged that the packing profile data relating to said desired output will detail the desired temporal profile of the output from the analysing means during the packing process.

It is envisaged that it will be possible to provide the packing profile data on a portable data device such as a smart card or a floppy disk.

Preferably the system for packing the chromatography column is capable of taking inputs from a plurality of receivers/detectors. It is envisaged that each may be located at a different height on the chromatography column.

Preferably the system has a plurality of analysing means, each respective analysing means for analysing a signal from a respective receiving means and generating a result based upon said analysis. Alternatively the system may have an analysing means capable of analysing a plurality of signals received by a plurality of receiving means and capable of generating an output or a plurality of outputs based on analysis of said received signals. Preferably the pump control means is capable of receiving a plurality of outputs from one or more analysing means and controlling said pump on the basis of said outputs.

A further aspect of the present invention is a chromatography column with an attached sonic transmitter or transceiver for transmitting a sonic transmission into the interior of the chromatography column.

A further aspect in the present application has to do with packing a chromatography column. In our work we have found that although a sonic transmission can be affected by the packing density and pack quality of a bed, these effects are more difficult to detect reliably than the simple large effect on the transmission due to the presence, as opposed to the absence, of the bed (settled or packed media). The latter is a strong change and easily detected, so that the position of the bed "front" can be determined with confidence using such sonic transmissions, even when (as is strongly preferred) the sonic transmitters/receivers are outside the column interior and must act via the column wall. At the same time we have made a new and useful finding that the rate of advance of the bed front during packing is a significant parameter correlating with the quality—in particular the quality in terms of plate value i.e. chromatographic efficiency—of the resulting pack. This is of practical importance because of the difficulty of standardising pack control parameters. For practical reasons the conventional primary control parameter is the packing pressure applied by the pump at the packing port, and packing operatives are accustomed to adjusting this packing pressure during the procedure to achieve desired results. However the absolute values and profiles of the packing pressure for packing a given medium into a given column cannot usefully be prescribed. This is because different column set-ups, even with essentially identical columns and media, generate significantly different back-pressures associated with variations in slurry concentration, bed support type, buffer viscosity, temperature, column expansion and the flow systems downstream of the bed, e.g. length, diameter and the number and acuity of bends in pipe work. In practice, several trial packs followed by plate value assessments are needed before an optimum packing pressure profile can be settled on for a given column set-up.

A constant packing pressure is not a useful control. In general the flow will be found too high in the early stages. Conversely if fluid flow is held constant the pressure at the end of the procedure is too high for good results. These subtleties are peculiar to closed-column, injected slurry techniques; they do not arise in the conventional open-column pack where essentially all the medium needed for the pack is present in or above the column space at the outset.

Thus we propose a method of packing a chromatography column in which the rate of advance for the bed front is measured and one or more packing parameters—typically pump speed and/or slurry concentration—controlled in dependence on the measurement to approximate the ongoing rate of advance to a target value, or to keep it in or bring it into a target range.

In line with the aspects above, the preferred method of measuring the rate of advance of the bed front is by detecting successive positions of the bed front using sonic/ultrasonic transmissions through the column interior.

Typically the preferred (target) rate of bed front advance will vary during the pack. The method may involve measuring that rate at plural positions distributed axially (i.e. in the direction of accumulation of the bed) along the column. Control feedback can be arranged by means of conventional processing technology, feeding the output from the relevant sensors, e.g. ultrasound receivers to a control processor for calculation of the real-time rate of advance, comparison with a target value representative of a desired rate of advance or "profile" (variation with time, or with axial location) of the rate of advance, and control signals sent to a pump to determine or vary the rate of pumping accordingly.

Because this method takes direct account of the actual accumulation of the bed, it can avoid some of the trial and error preparation which (for reasons explained previously) is associated with control via monitoring the packing pressure.

While the optimum advance rates and advance rate variation patterns can be determined previously for given columns, liquid and media, it can be said in general that a preferred "rate of advance" profile will usually have a first phase, corresponding to an initial build-up of medium on the bed support (mesh or sinter), which is slow by comparison with a subsequent main phase which is faster. There may be a gradual increase between the two. This appears in general to lead to better packing results. The difference if any between the rates of advance during the main phase of packing and at the final phase of packing (where the bed approaches the top permeable retainer e.g. mesh or sinter) appears to be less critical. It may be of importance with some media in which case the target profile can be determined accordingly. People packing similar media into similar columns subsequently can then get the benefit of that initial empirical investigation on an automated basis.

A skilled person will appreciate that for the present purposes it may be preferable to have an essentially progressive assessment of the rate of advance of the media front up most or all of the axial extent of the column interior. To this end a series or array of sonic transmission and detection elements e.g. piezoelectric elements may be installed on the chromatography column, preferably on the outside of its wall so as not to affect the uniformity of the interior. The direction of transmission of the signals from transmitter to receiver is preferably substantially transverse to the direction of advance of the bed front, since this maximises the difference in effect of the transmission in front of and behind the front. However, other dispositions of sensors and transmitters may be acceptable. For example, an emitter or receiver may be positioned at the end of the column opposite to the end where the bed initially accumulates. It may transmit to or receive from sensors or transmitters disposed on the side of the column. Or, such an arrangement may be combined with a transverse (radial) system; the two systems may reference one another for reliability. And/or, the rate of advance of the bed front may be determined by directing a transmission axially or with an axial component, onto the bed front and detecting the back-reflection from the front. In the latter respect, we note that the use of ultrasonic transceivers to determine the levels of materials in industrial vessels is established practice. Indeed, it has been used in the specialised context of a fluidised bed chromatography column as a means of measuring the height of the particle bed in use. However, these transceivers project laterally inside the column which is acceptable in liquid-containing vessels, and in fluidised bed chromatography processes which are exceptional in that the medium does not fill the column in use, but is not good practice in packed chromatography bed procedures. Also, the prior art uses of ultrasound transceivers in vessels have not been used to control the rate of advance of a bed front on a feedback basis. There has not previously been any perceived reason for doing so.

The sonic/ultrasonic transmission apparatus may have separate emitters and receivers, or transceivers which combine the two functions. These technologies are in themselves well known, as are arrangements for positioning sonic emitters and receivers effectively on the outside of the vessels so that they will work through the wall. The latter technology is well established in ultrasonic meters which measure fluid flow rates in pipes using Doppler-type effects.

Apparatus for carrying out the method is a further aspect of the invention. In particular the apparatus may comprise a chromatography column adapted with suitable sensors and control circuitry operatively connected to a packing pump to carry out a method as described. A particular apparatus may include an array of sonic sensors/transmitters mounted on (or adapted to be mounted on) a column wall and connected to electronic processing means programmed to determine a rate of advance on the basis of signals from these sensors, compare the rate of advance with desired targets or ranges and, in dependence on the result of the comparison, send or adjust control signals to a packing pump.

A further aspect of the invention is based on a further new finding we have made, which is that the presence of adventitious substances in a packed bed can affect the speed and/or attenuation of sonic transmissions through the bed. It is therefore possible to use such sonic transmission to detect the presence and/or the movement in the bed of such materials. In one aspect such materials might be contained in bands gradually eluting through the bed during a chromatographic process. Using one or more sensor arrangements to detect the passage of such a band at one or more corresponding regions of the column enables a "tracking" of the process which can be helpful to the operator in monitoring the procedure and collecting the separated substances as they emerge. With sufficient sensors, e.g. a series or array as discussed above, the movement of a band of substance through the column can be tracked, and if desired visualised on a display outside the column.

Another use of this finding is as follows. In some processes the materials presented to the column for separation include materials which will bind irreversibly to the chromatographic medium in the column. Generally these bind to the medium immediately or soon after entering the bed. Their permanent binding reduces the transitory binding capacity of the medium which is the foundation of the chromatographic process for the other components of the mixture. A region in which the bed is progressively less and less effective grows gradually adjacent that end of the column at which the starting material is introduced. In practice there comes a point at which the affected band at the end of the bed is so large that the bed as a whole is inadequate. This usually becomes apparent when sooner or later a product batch proves to be impure. The processing of that impure batch is a substantial waste of time and materials. The present invention therefore provides a method in which, by means of sonic transmissions through the relevant part of the bed, it is determined from time to time whether such permanently-bound adventitious substances have reached a predetermined threshold position in the column corresponding to an operational limit at which the column needs to be emptied and repacked. This procedure promotes confidence and consistency which are of high importance with these technologies.

A final aspect disclosed herein relates again to packing rather than running the column. During the packing process, sonic transmissions according to any of the above proposals are used to identify a time at which the advancing bed front has nearly reached the top of the bed space. In dependence on that detection, the control system switches the pump control to act in dependence on a detected packing pressure.

When a dip in packing pressure characteristic of complete packing is observed, the pump is turned off. Correspondingly programmed apparatus is again an aspect protected herein. To explain: it is well known to those skilled in packing chromatography columns that a characteristic dip in packing pressure is seen just as the column becomes full. It is undesirable to continue to apply the pump beyond this stage; a better pack is obtained if it is promptly turned off. With an opaque column, the packing operator must keep a careful watch for this. A continuous pressure-sensitive control of the pump is not desirable, however, because pressure fluctuations of comparable sizes occur at other stages of the packing when the pump should certainly not be turned off. By using a sonic transmission sensor to note when the bed is nearly complete and only then initiating the monitoring for a pressure dip, the virtues of these respective techniques are happily combined.

Tests underlying the present proposals, and examples of apparatus and procedure, are now described with reference to the accompanying drawings.

DETAILED DESCRIPTION OF PREFERRED EMBODIMENTS

Figure 1:
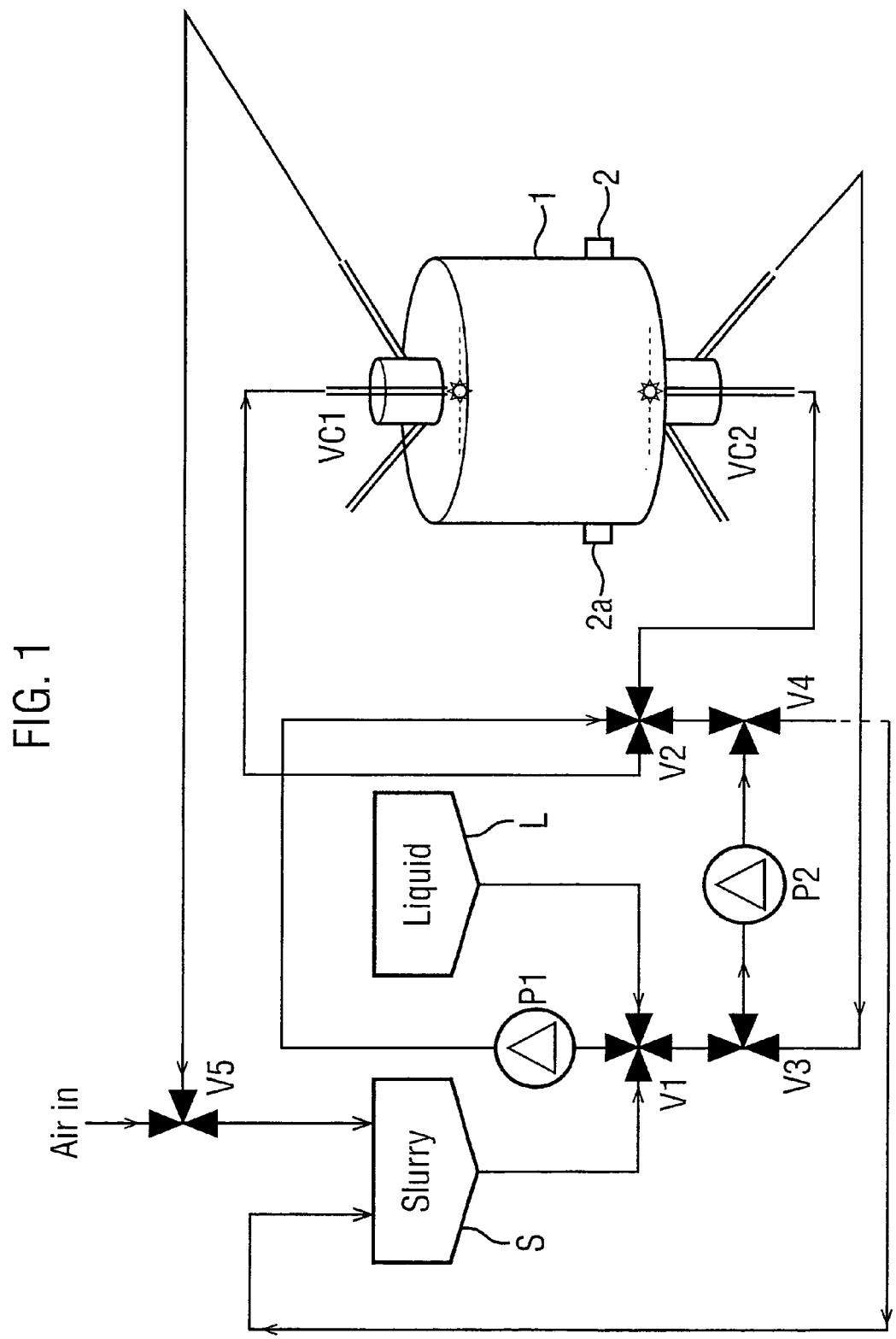
FIG. 1 is a schematic view of a chromatography column with an automated packing system.

With reference to FIG. 1, a chromatography column 1 is provided with upper and lower packing valves vc1, vc2 of the kind described in our WO-A-96/10451 to which reference should be made. The packing flow system includes a larger pump p1 for packing and for spraying the column top when unpacking, a smaller pump p2 also for packing and enabling suction from the bottom of the column when unpacking, tanks S, L to hold a slurry of packing medium and particle-free liquid respectively, a four-way valve v1 controlling the inlet to the pump p1, a four-way valve v2 controlling the outlet from the pump p1 as between the top and bottom of the column, a three-way valve v3 controlling the inlet to the pump p2 from the column or tank, a three-way valve v4 controlling the outlet from the pump p2 to the column or the tank, and a three-way v5 controlling a return from the column top to the tank or to a vent. For a description of a suitable enclosed (injected) packing procedure, refer to e.g. WO-A-96/10451, GB-A-2258451 or WO-A-99/64130 as mentioned previously.

In the present work the column was a variable-length 600 mm diameter column, operated at a bed height of 160 mm.

Test 1: Recognising the Front

Figure 2:
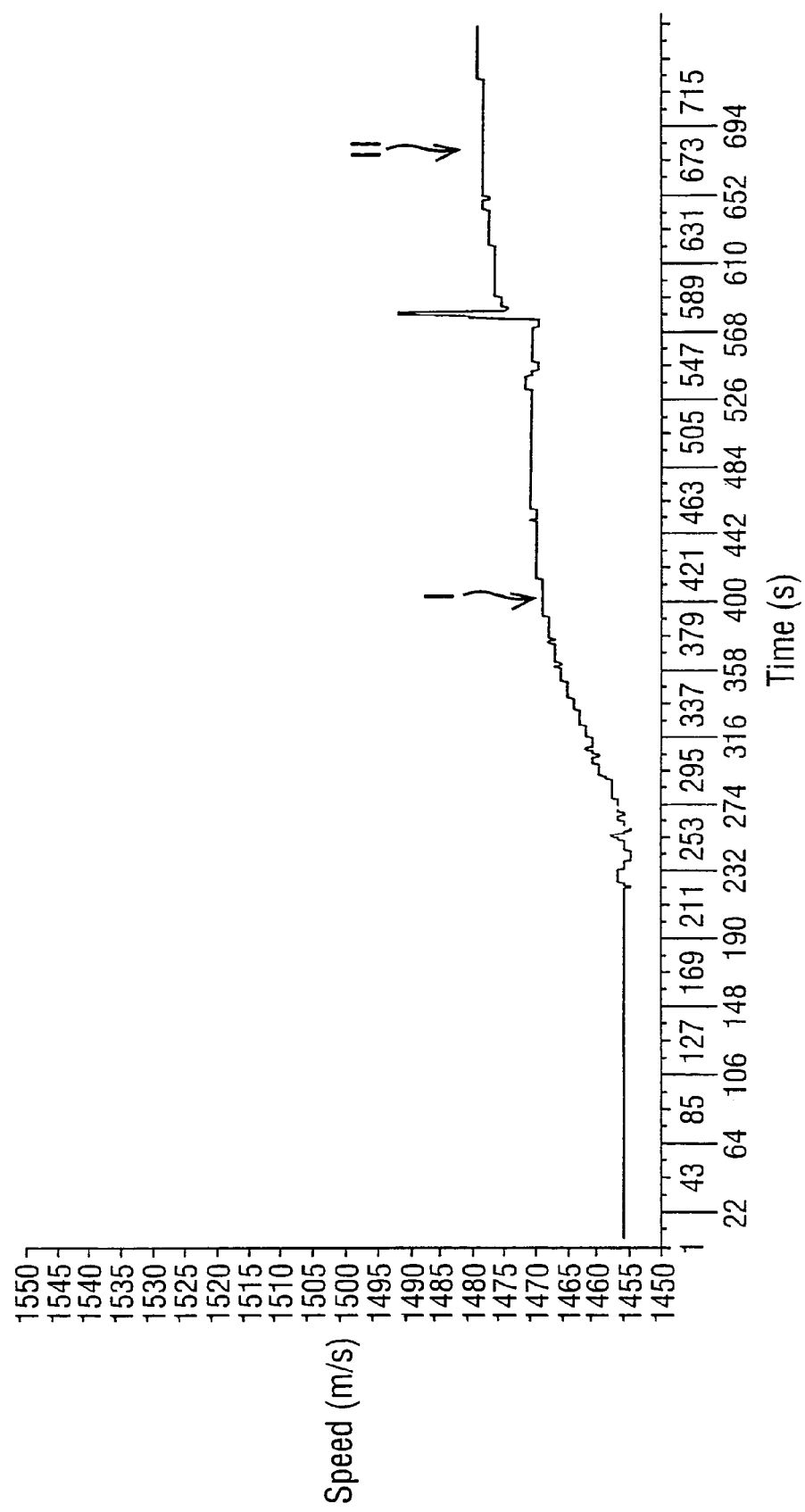
FIG. 2 shows ultrasound speed measurements across the column during a trial pack.
Figure 3:
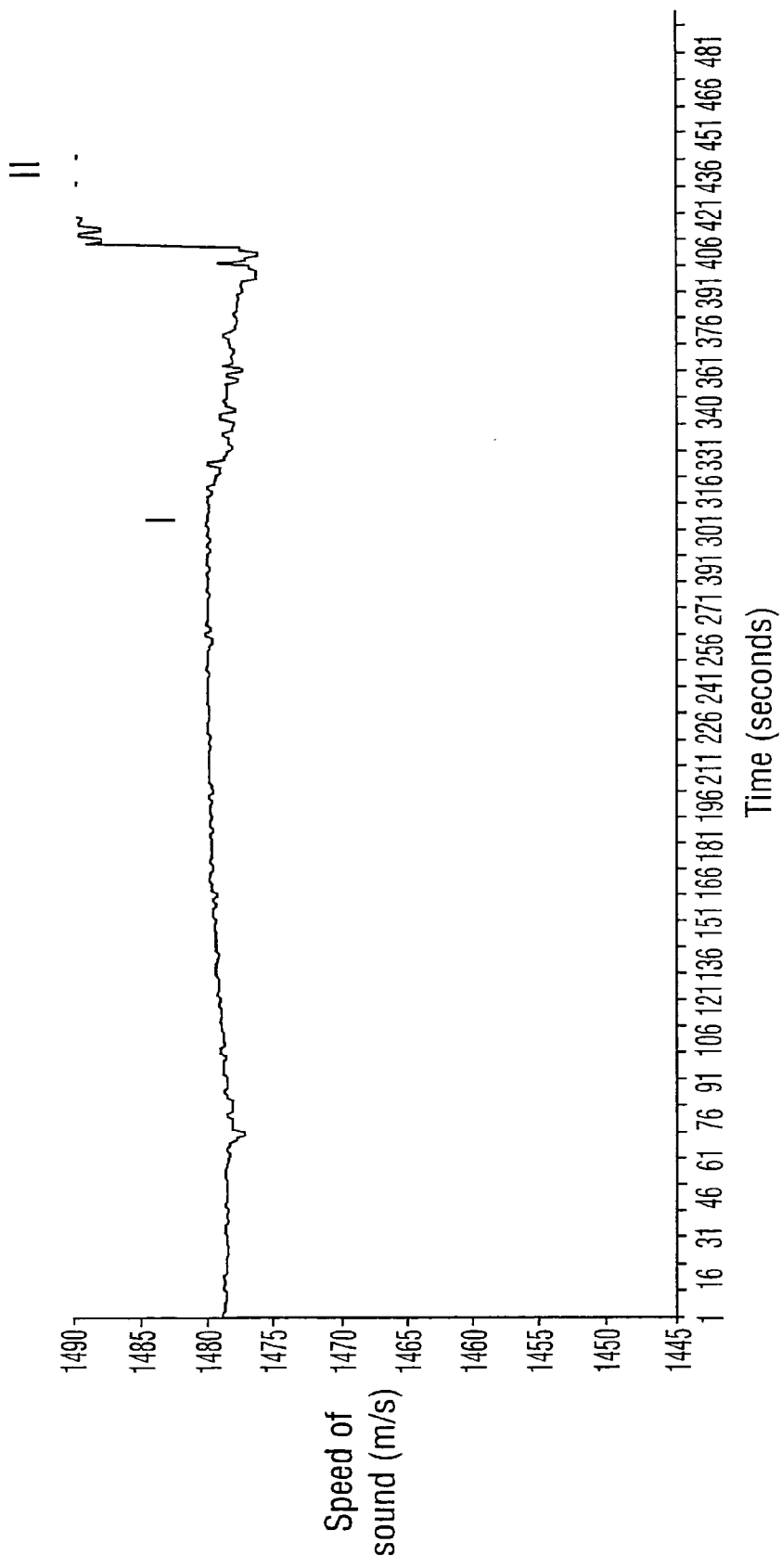
FIG. 3 shows similar measurements but with a greater degree of temperature control.

In a first set of tests Sepharose 4 medium was used, slurried in distilled water. By way of illustration, the following Table 1 shows the variation of various parameters as the pack proceeded. Ultrasound transceivers 2,2a (FIG. 1) were secured to the outside surface of the column wall about a third of the way up the bed. The speed of sound through the column interior as measured between these is given in Table 1. The tabled values are purely illustrative. FIGS. 2 and FIGS. 3 show plots of the sound speed between the ultrasonic transceivers 2,2a and time in two different runs. FIG. 2 shows an initial phase I during which the sound speed increased gradually, followed by a discontinuity at which the advancing bed front rose past the transceivers—the column used was a transparent-walled-one for reference, so this was seen to happen—and a second phase II where the sound speed through the medium bed was appreciably higher. Sound speed is significantly dependent on temperature. Investigations showed that the gradual rise in phase I was due more to temperature changes than slurry density phenomena. Indeed, more scrupulous temperature control of all the materials resulted in the FIG. 3 plot where the speed of sound through the unpacked region of the column remained essentially constant until the clear discontinuity when the bed front rose past the transceivers 2, 2a. These experiments confirmed the ease of identifying the bed front using ultrasound.

Test 2: Quality of Pack, and Accumulation Rate

A further set of tests was then carried out using a ceramic medium. The study and its results were as follows.

SUMMARY

Ceramic medium (BioSepra Q Hyper DF) was packed into a 400 mm diameter column to a 200 mm bed height. The buffer, packing pressure and slurry concentration were varied. The two best repeated results were obtained by 0.025M Tris HCl adjusted to Ph adjusted 7.5 with NaOH. The slurry concentration was 50% and the end packing pressure in the column was 1.5 bar. The flow rate at the start was initially 1000 cm/hr.

In the light of our work, it appears that at the start of the pack the bed height build should be at say from 25-30 mm/minute for the first third of the total packing time. After this stage the rate should increase to for example 75-80 mm/minute until the column is filled. For a 200 mm bed height, near the completion of the pack of the flow may be pulsed between 300 and 900 cm/hr. The pack can be considered complete when the pump stalls, usually after 3-4 minutes for a 200 mm bed height.

It appears from the work (described below) that there is a packing rate "corridor" in terms of rate of bed height accumulation which has an appreciable width and which if kept to can lead to a better pack. An actual packing rate/time path following such a corridor can be regarded as a fingerprint of an optimised packing process. That is to say, if the packing operative keeps the packing parameters so that the rate of bed accumulation is within the upper and lower bounds of the prescribed "corridor" then a good pack can be predicted. This "fingerprint" or pack profile can then be used in production as a practical aid via automation and as a validation parameter for a column.

DESCRIPTION OF WORK

The column used was a variable bed height Mark II Euroflow column (EQ400-V-EQ911, with steel meshes). The medium has already been identified.

Before packing the medium was de-fined three times in slurries at about 30% concentration. The slightly cloudy supernatant was pumped away. The column was fully primed with buffer before all packs. Slurry was pumped in via the top nozzle (it can be done through the bottom) and the slurry liquid left via the mobile phase path at the bottom of the column. The packing pressure was measured at the top mobile phase port. The slurry was pumped by a Husky 715-diaphragm air-driven pump.

Bed quality evaluation was by injecting one litre of a 1% acetone solution in water under the column using up flow and down flow at a variety of flow rates, before and after an 18 hour test period for bed stability. The same was done with mobile phase in 0.025 M Tris HCl adjusted to pH 7.5 with NaOH.

Table 2 details the 13-stage test conditions used. Table 3 displays the 100 cm/hr flow rate (21/minute) results based on the lowest HETP, being those obtained nearer the 100 cm/hr results. Results are shown for before and after the stability test delay.

Figure 4:
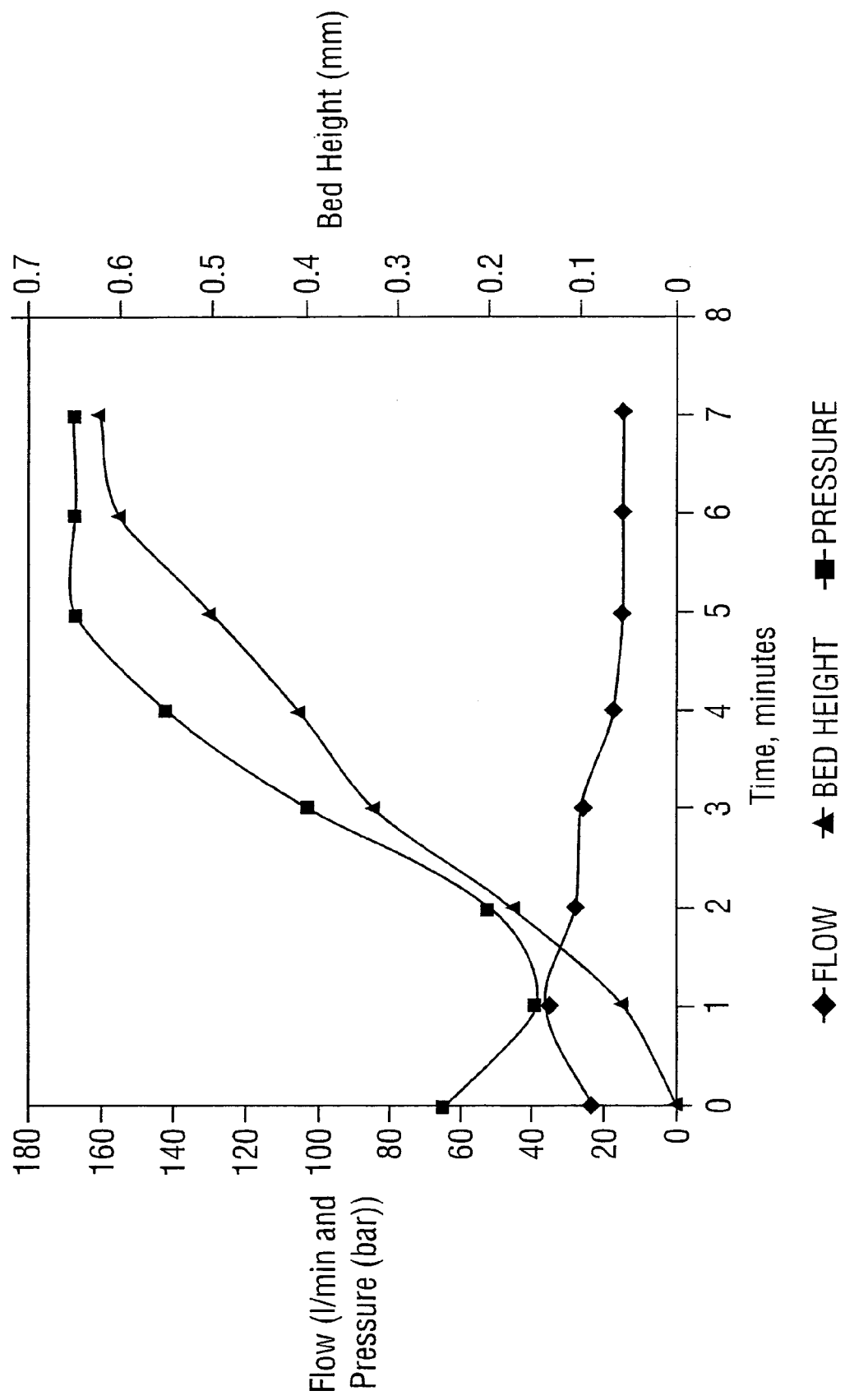
FIGS. 4, 5, 6 and 7 are data showing relations between pack parameters and pack quality for a Sepharose (gel) medium.

FIG. 4 of the drawing shows the packing profile for each of the five packs indicating the quality (in terms of plates) of the pack achieved. The graph shows the rate of build-up of the bed during packing; this rate of build up is of course a complex result of flow and pressure conditions in the column during packing at the relevant stage.

The results indicate that the ceramic medium could be packed in the 400 mm diameter column to a 200 mm bed-height to a quality of over 4000 plates per metre with asymmetries of about 1.4. Two repeats gave similar results.

Figure 5:
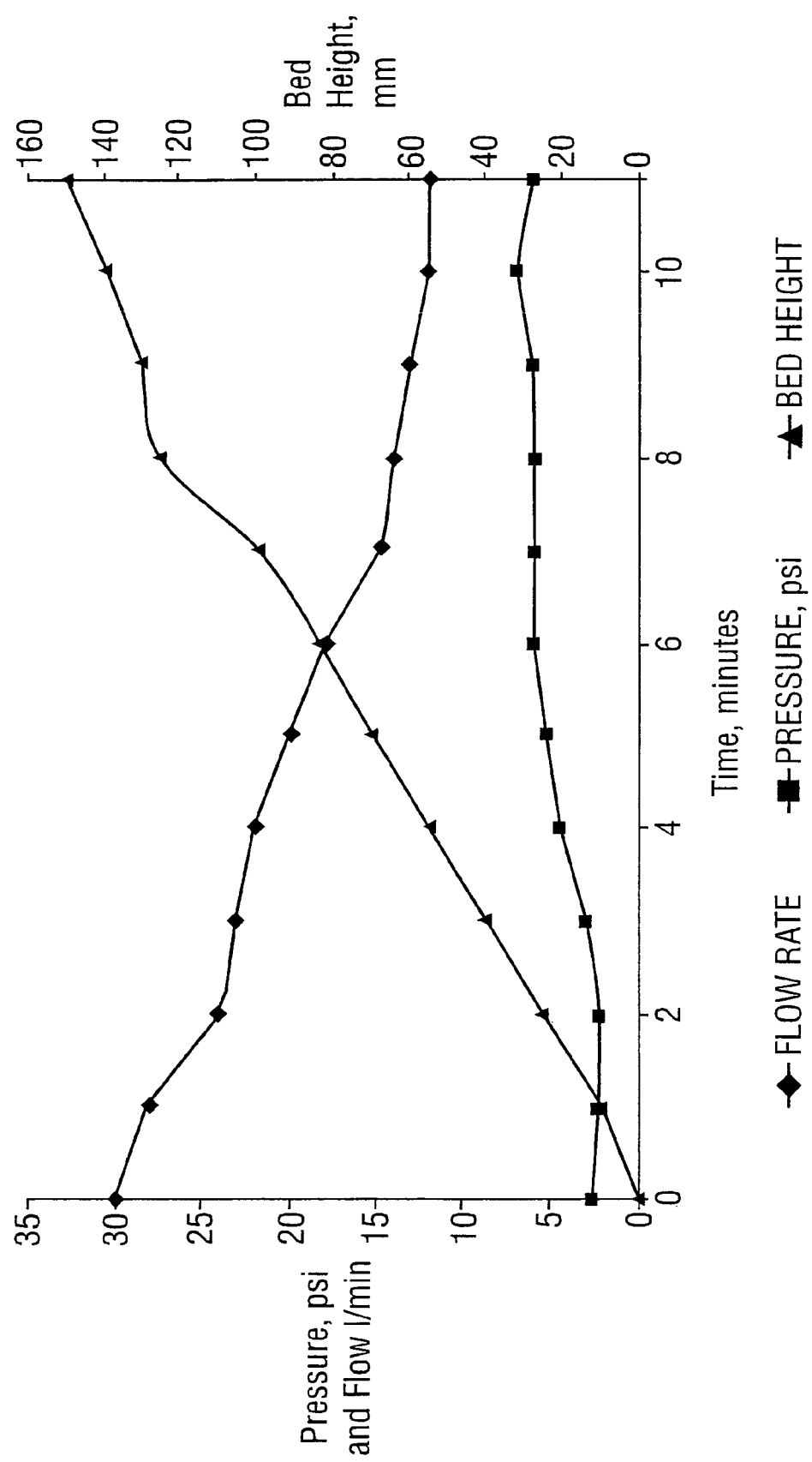
Figure 6:
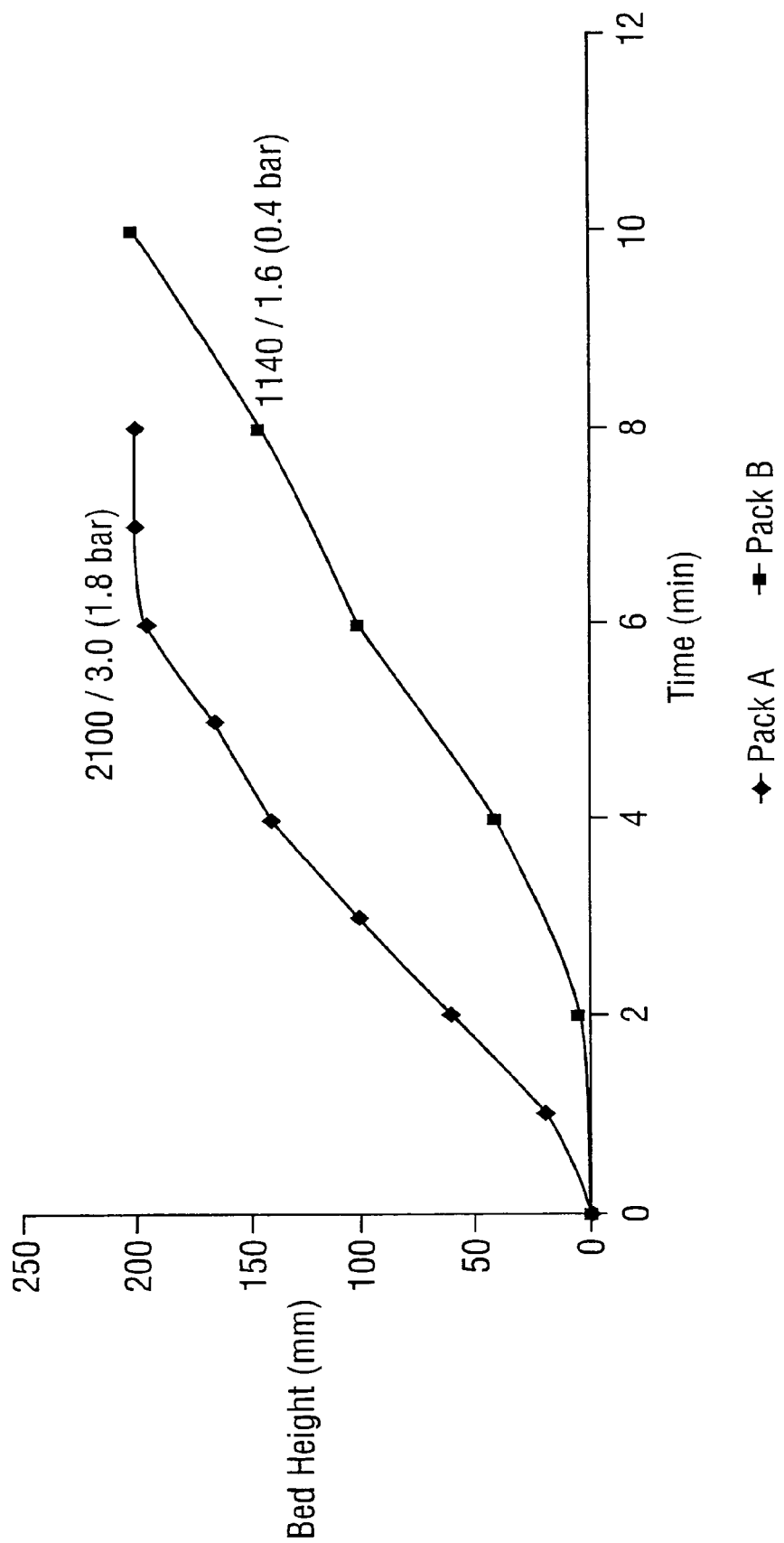
Figure 7:
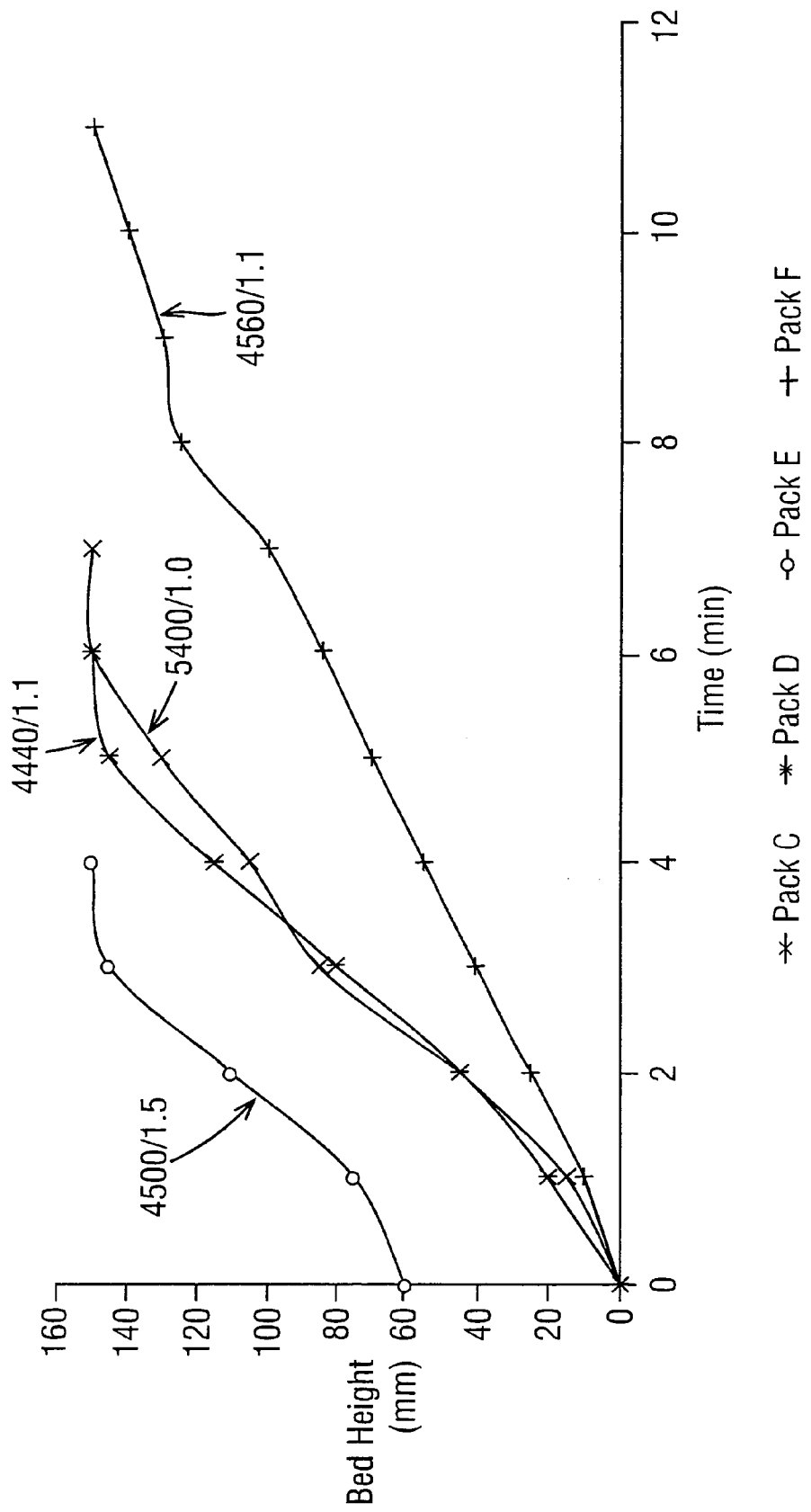
Figure 8:
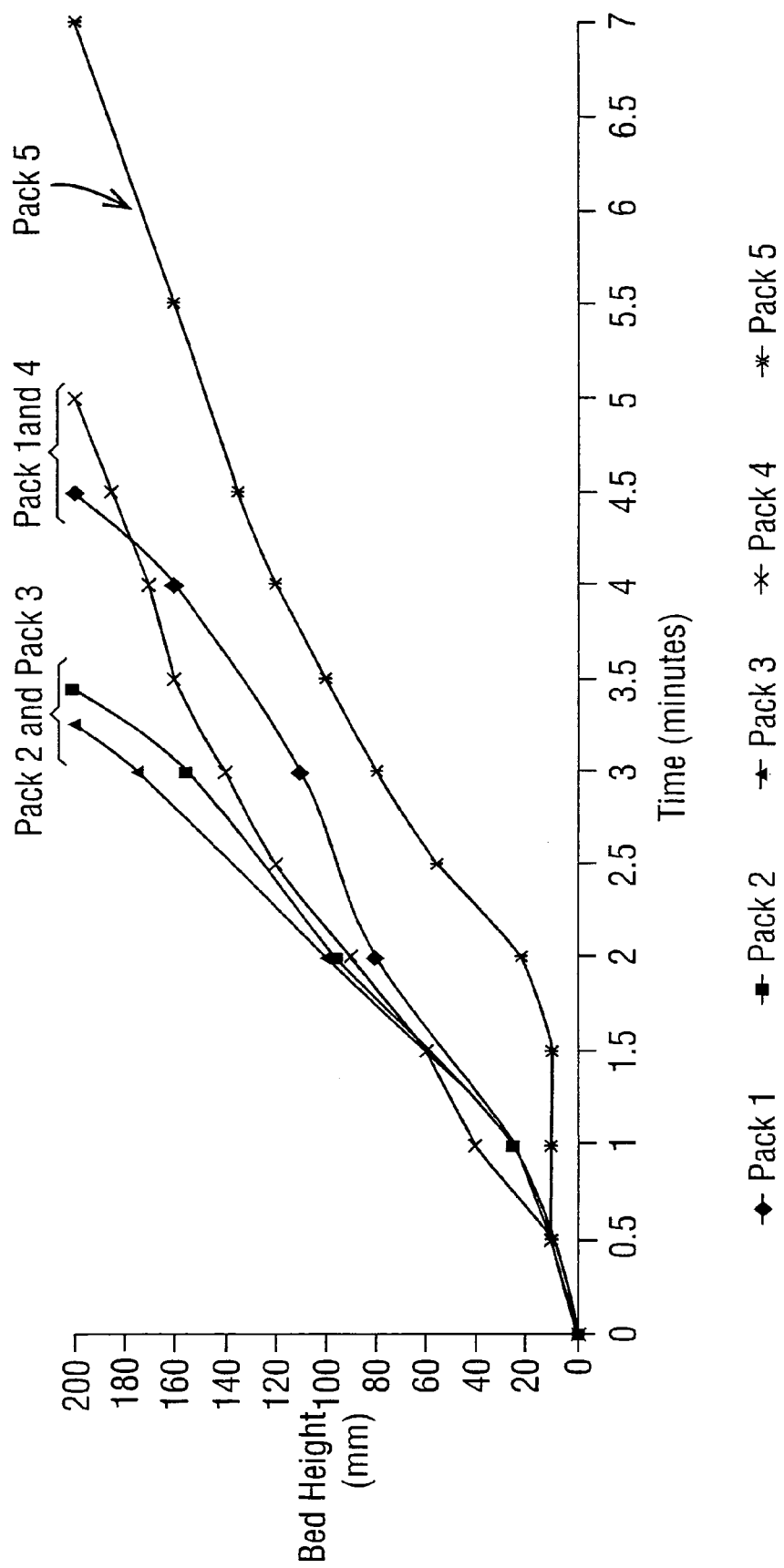
FIGS. 8, 9 and 10 are packing data from 5 runs for determining a relation between packing rate and pack quality for ceramic media.
Figure 9:
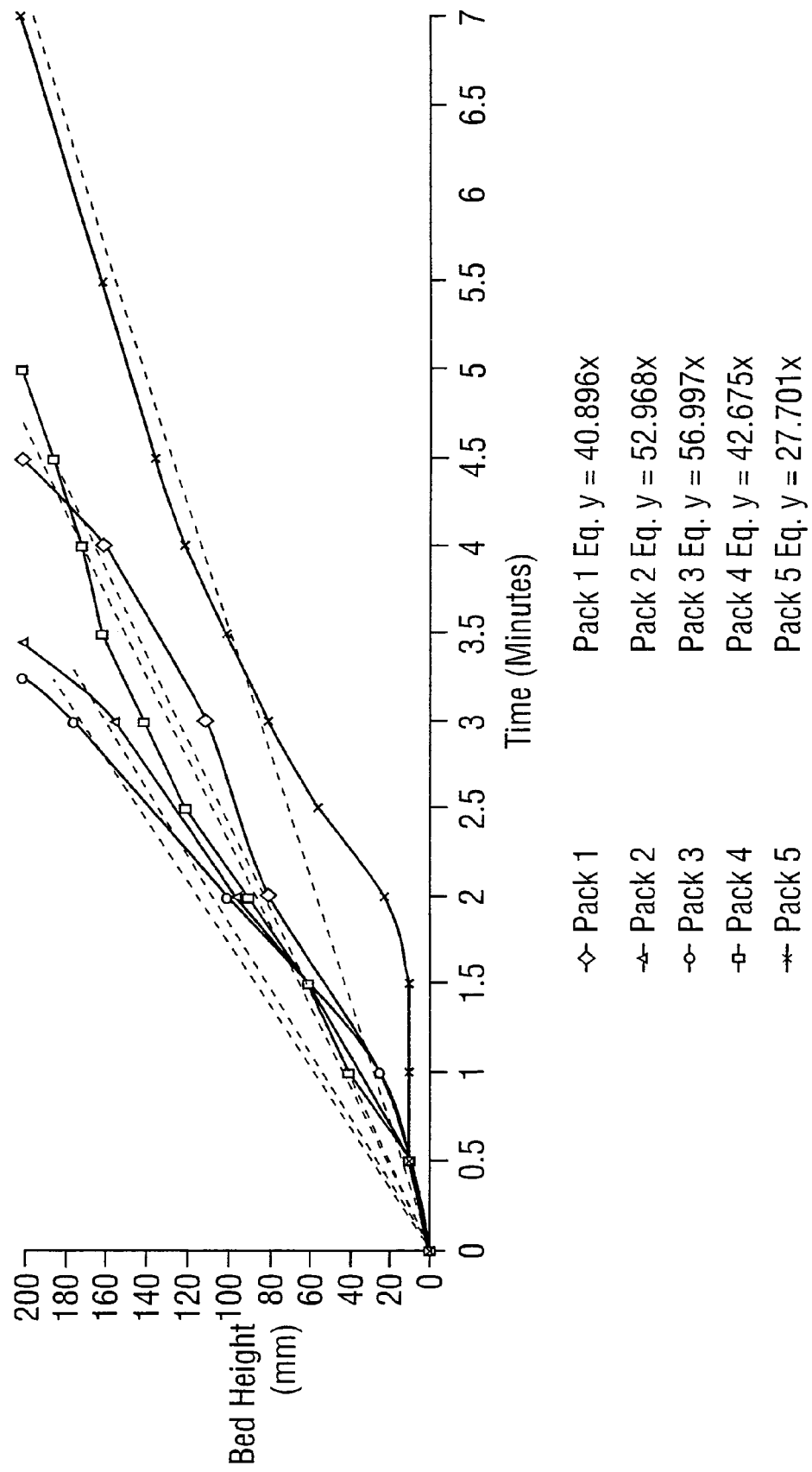
Figure 10:
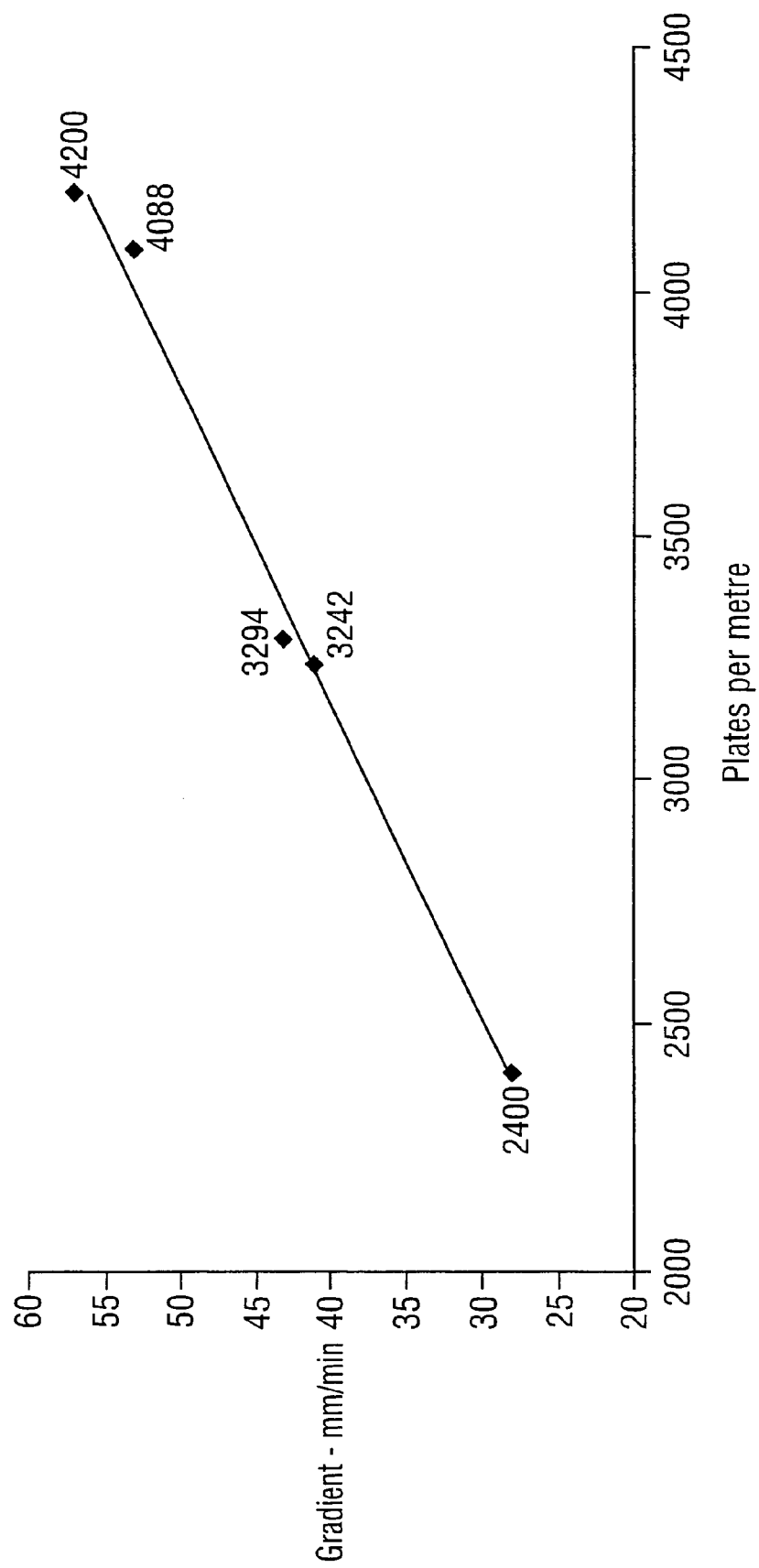

FIG. 5 adds to FIG. 4 by including linear regressive approximations to the respective curves, and their radiance. FIG. 6 shows that there is a correlation between the gradient (i.e. the rate of bed build-up in mm/minutes) and the plate number (quality) of the resulting bed.

Of course these straight-line regressions are crude approximations. Table 4 below gives a better analysis by dividing the packing procedure into 3 stages.

Observations from Table 4 are listed below.

1. The 'good' packs (Pack 2 and 3) share very similar rates at start middle and end. The first build up of the bed is the slowest part. Then the rate at which the bed builds increases at Phase 2 perhaps because the supernatant slurry concentration increases. This higher rate is held constant for Phase 3.
2. The 'satisfactory' packs (Packs 1 and 4) deviate from the successful profiles significantly at the later part of the pack. Their initial build up rates are quicker than the 'good' packs. Their $2^{nd}$ and $3^{rd}$ Phases are very different yet they yield similar results.
3. The 'poor' pack (Pack 5) profile deviates the most from the others. The initial build up is low or similar but the $2^{nd}$ phase is 4 to 8 times slower. Phase 3 increases but is still half that of the Phase 3 rates of the good packs.

Some conclusions based on these observations are listed below:—

1. During the first phase where media initially builds up on the bed support the rate needs to be slower than the later Phases. Perhaps to avoid blinding the mesh with high velocity media that has little or no back pressure.
2. If the $2^{nd}$ Phase is equal or slower than the $1^{st}$ Phase the result is very poor (Pack 5). Perhaps the slower rate allows the layer against the bed support to mix and lose its packing density or homogeneity. Thus a quicker $2^{nd}$ Phase rate is needed to hold down the $1^{st}$ layer.
3. The $2^{nd}$ Phase can be very different to the $3^{rd}$ Phase and still yield satisfactory packs (Packs 1 and 4)—it is not catastrophic.
4. To achieve better packs the $2^{nd}$ and $3^{rd}$ Phases are preferably about three times faster than the $1^{st}$ Phase. They may be at about the same rate. This may helps homogeneity throughout the rest of the bed.

Based on these results it appears that there is a packing rate 'corridor' of varying width that can be followed to achieve a 'good pack'.

Figure 11:
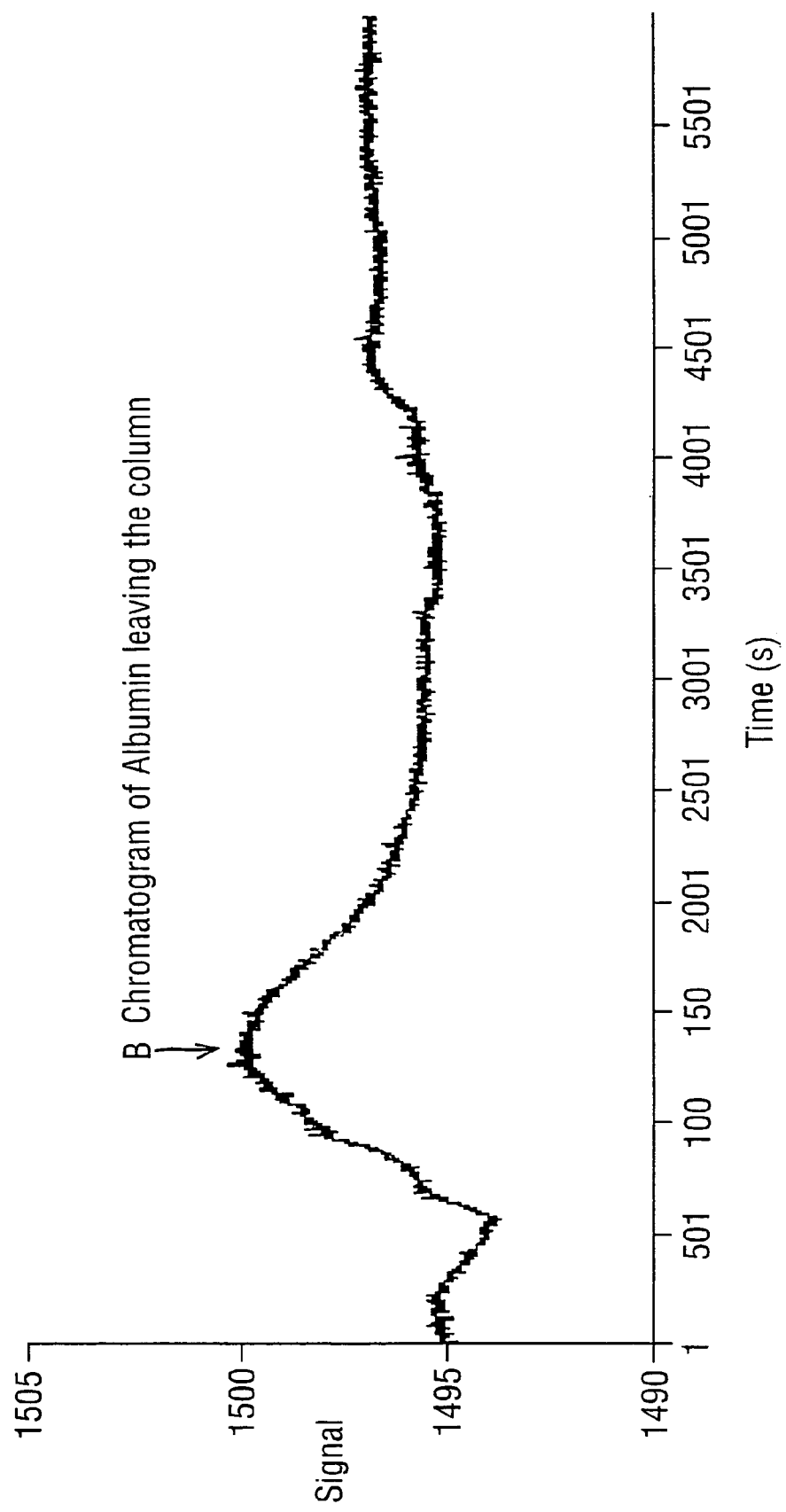
FIG. 11 shows a UV trace at the product outlet of the column in a test run with a sample of albumin.
Figure 12:
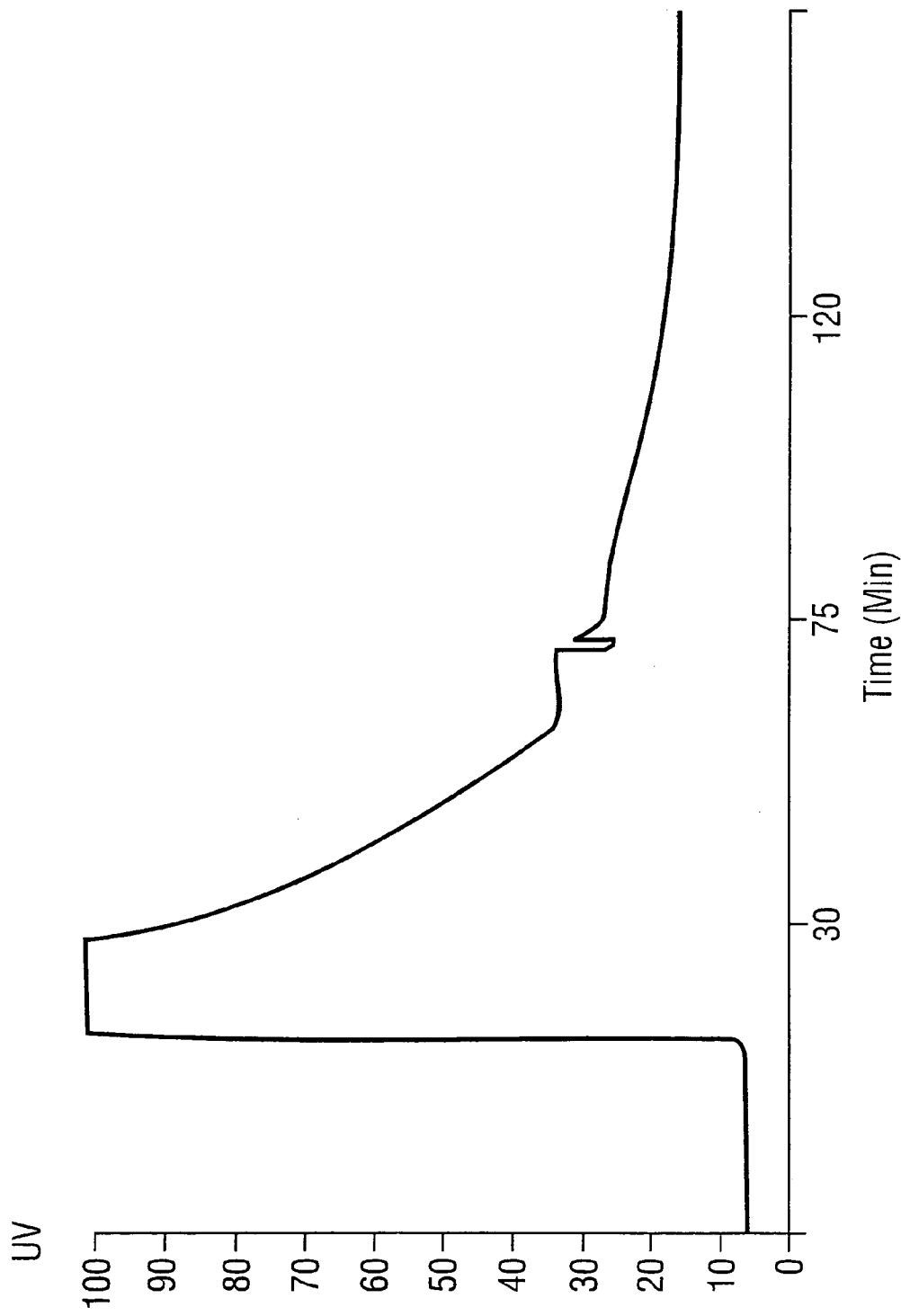
FIG. 12 is an ultrasound speed trace during the same run, showing a speed change through the albumin-occupied region of the column.

FIGS. 11, 12 show the result of an experiment in which a column set-up as shown in FIG. 1 had applied to it a sample pulse of 10% albumin. FIG. 12 indicates that the albumin passed as a band or pulse through the column as detected by UV detector at the column exit. FIG. 11 shows the interesting results from the ultrasound sensor, namely that the passage of the band past the sensor correlated with a band of increased ultrasound transmission speed through the column. This is marked B.

Figure 13:
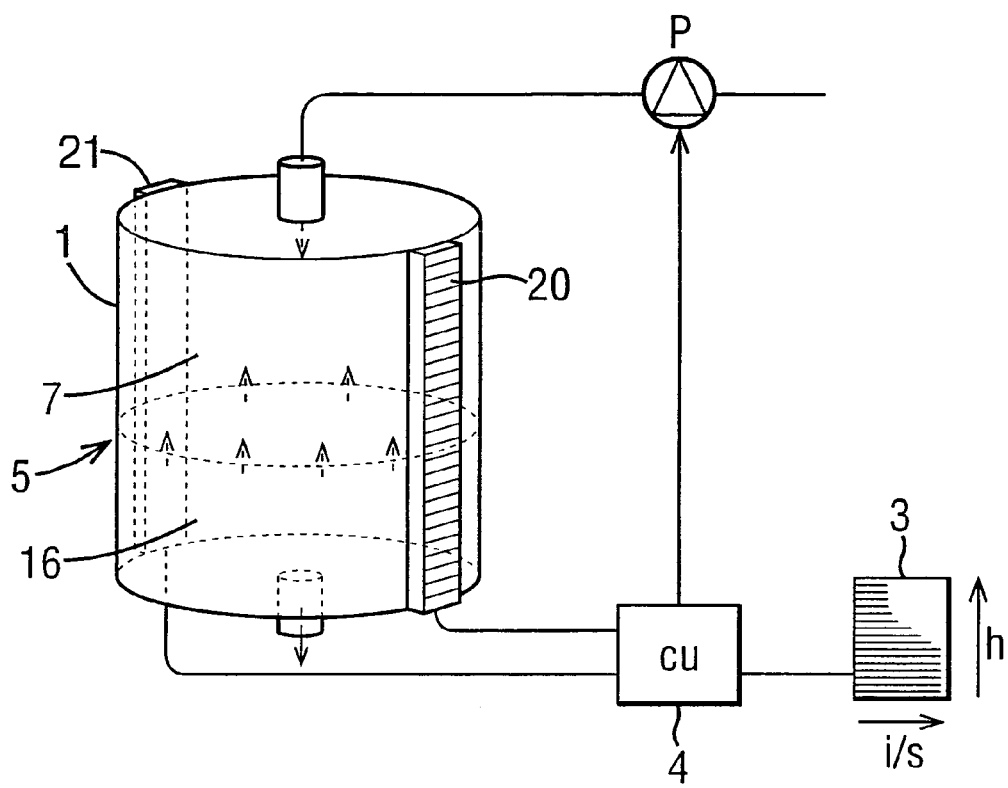
FIG. 13 is a schematic view of a column packing system exploiting feed-back from ultra sound sensors and having a display.
Figure 14:
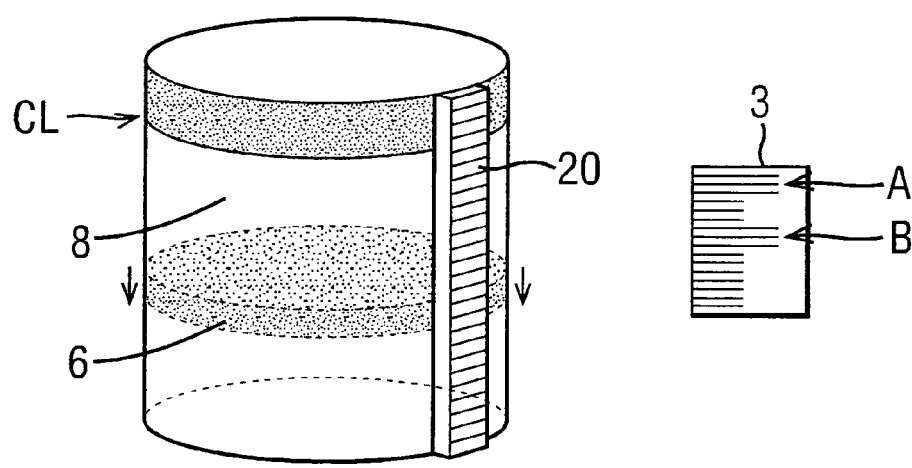
FIG. 14 is a further schematic view illustrating the detection of permanently-bound impurities and of sample bands passing through the column.

FIGS. 13, 14 show schematically an apparatus set up embodying the invention, with a linear array 20 of numerous piezoelectric transceivers applied up one side of the column, with a corresponding array 21 on the opposite side. They need not be exactly opposite; in particular a slight offset helps to avoid difficulties adjacent the ends of the column if there is a projecting central packing nozzle. The drawings show schematically the front 5 of a bed 16 rising up the column as packing proceeds. A programmed control unit 4—a conventional microprocessor—is fed with the inputs from the sensors and programmed with desired target data for the target rate profile. The packing pump P is controlled accordingly. An external display 3 is provided which may show the sound impedance or speed in bar form against the height up the column. FIG. 14 shows a similar apparatus being used at a different stage, when the column has been packed and is in use. One aspect of the use is shown at the top of the bed. A band of accumulating permanently-bound contamination is gradually extending down into the bed from the top. This affects the ultrasound transmission from the top sensors and is therefore shown on the display at 'A'. When it reaches a critical level CL the program issues a warning to the user that the column is effectively spent.

A band of material 6 is also shown, progressing down the column. This is material being purified. Despite the opaque column wall, its progress can be followed (peak B) on the visual readout of the ultrasound data.

FIGS. 15 to 19 show schematically these and other functionalities of the proposed column arrangement having the array of ultrasound sensors extending axially.

Figure 15:
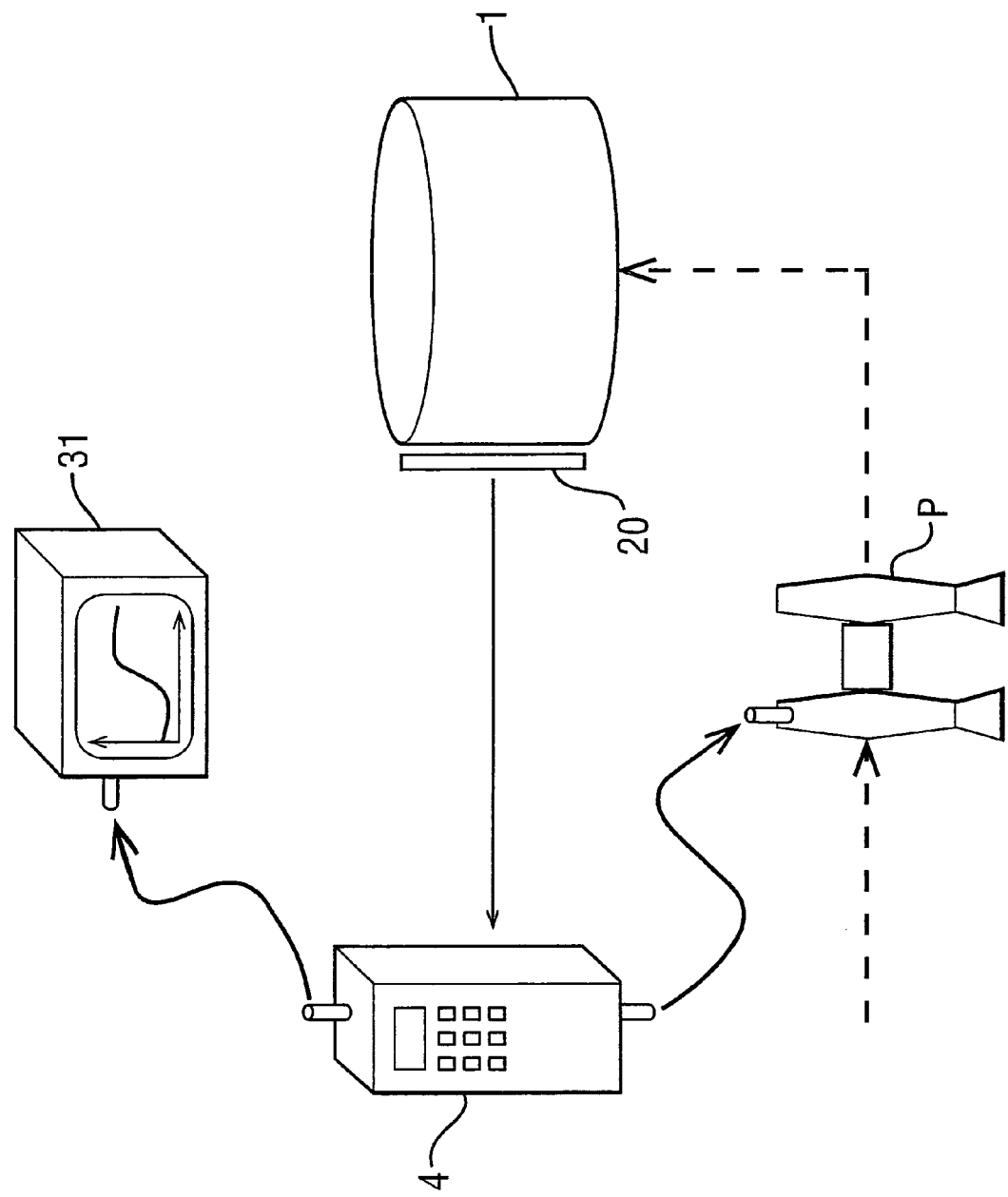
FIGS. 15 to 19 are schematic views of apparatus set-ups and procedures exploiting the ultrasound detection facility.

FIG. 15: column 1, sensor array 20, control processor 4, data logger 31, pump P. Basic 'fingerprinting' of a pack profile, plus pump control, using feedback.

Figure 16:
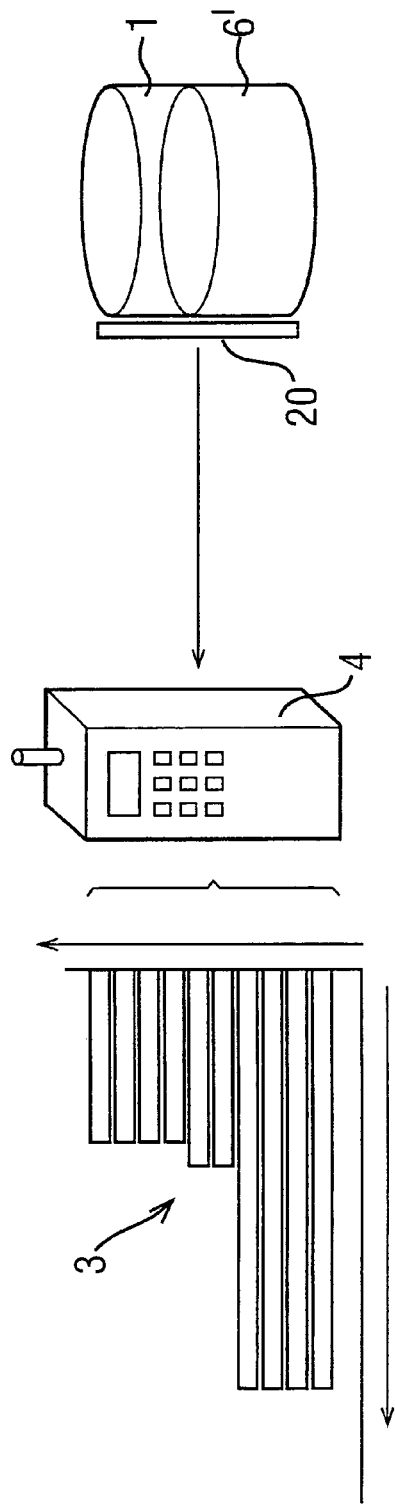

FIG. 16: packing, with tracking of the accumulating bed on display 3.

Figure 17:
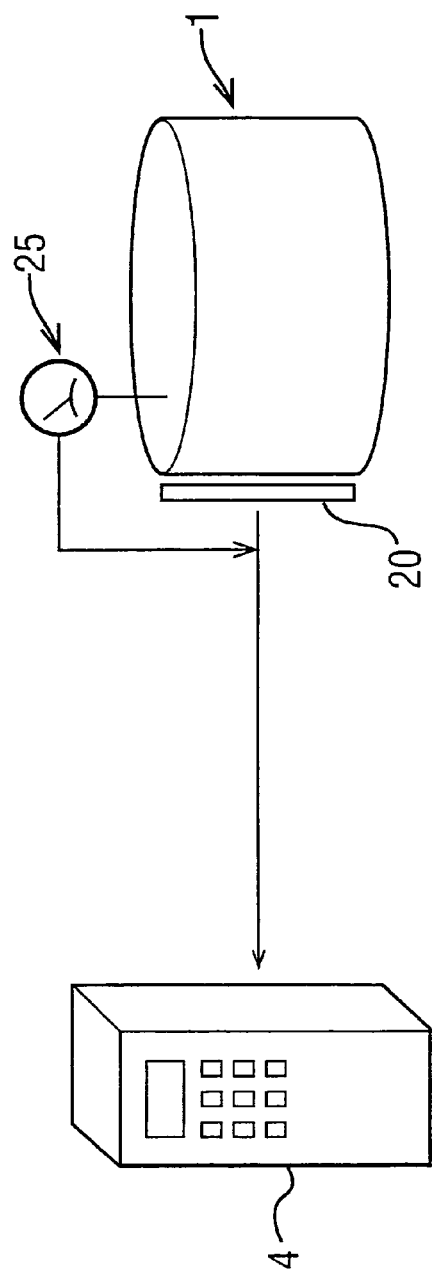

FIG. 17: packing method using additional control parameter of packing pressure at meter 25. Detect when column nearly full, open time window of sensitivity to pressure drop, pressure drop signals pack complete, pump stopped and valves moved to 'run' positions for chromatography.

Figure 18:
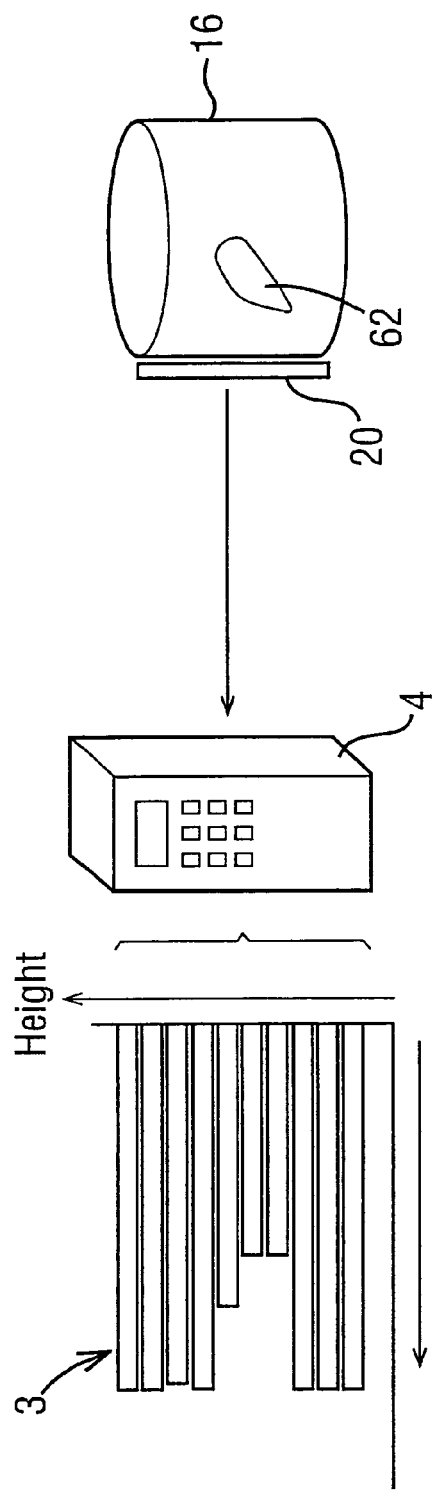

FIG. 18: display 3 indicating void or inhomogeneity 62 in the column contents.

Figure 19:
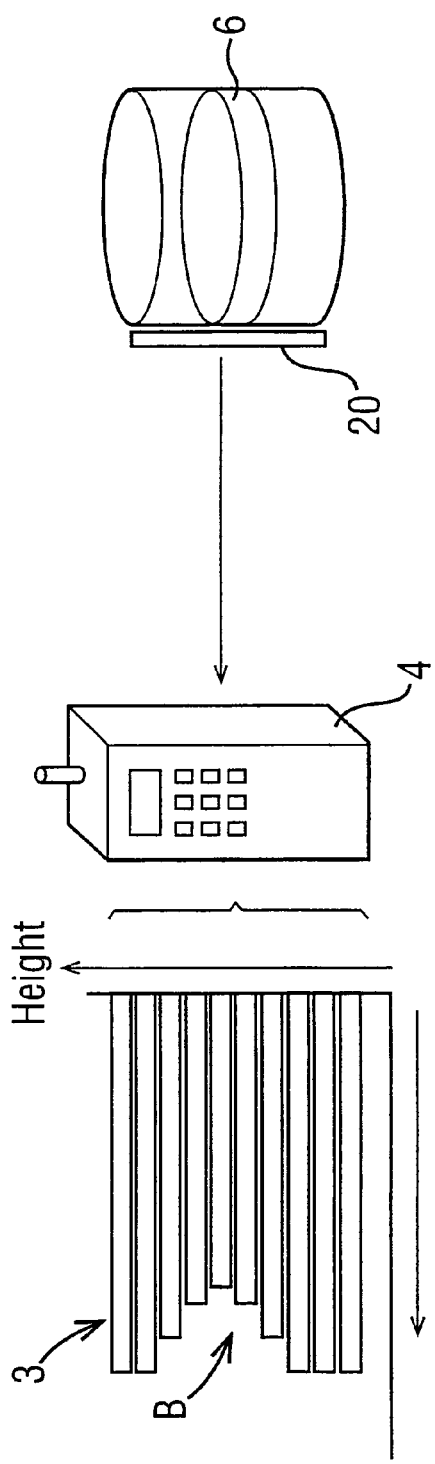

FIG. 19: tracking a band 6 of valuable component through the column display 3 or band 'B'.

Figure 20:
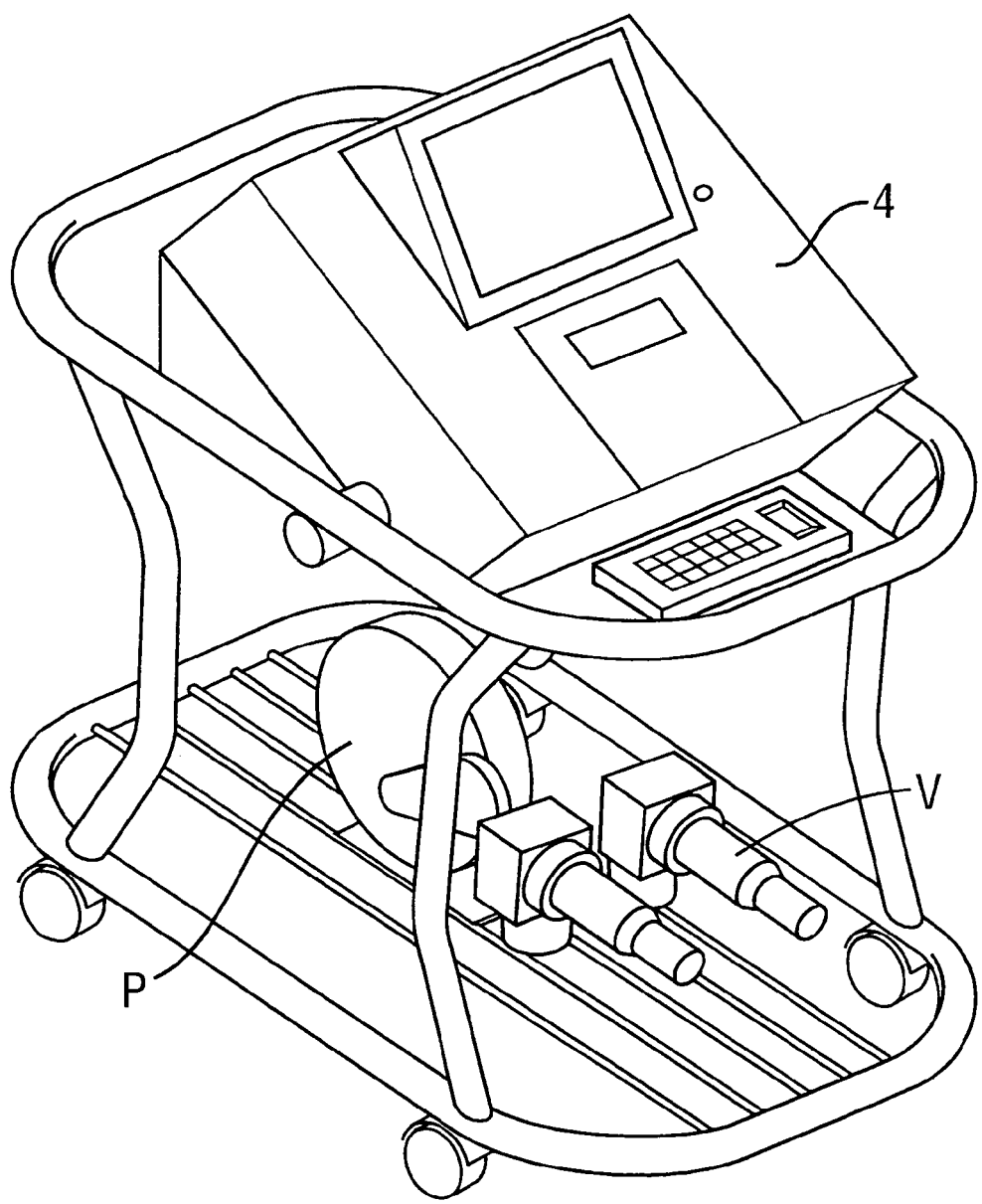
FIG. 20 shows a packing 'skid' embodying the invention.

FIG. 20: shows a packing station or 'skid' i.e. a movable trolley having a packing pump P and the associated valve connectors V, operatively controlled by processor 4 adapted to receive inputs from ultrasound detectors, initiate operation of transmitters, receive packing profile data and programmed to control the pump P accordingly.

TABLE 1

| SLURRY | 18° C. | COLUMN PRIMING LIQUID | 19° C. | AMBIENT | 19° C. |
|---|---|---|---|---|---|

PACKING PROFILE

| PACKING TIME minutes | FLOW l/min | Packing Air Pressure Baseline, bar Slurry through valve only PRESSURE bar | BED HEIGHT mm | Slurry through valve only bar MOTIVE AIR PRESSURE bar | SLURRY INLET PRESSURE bar | Speed of Sound |
|---|---|---|---|---|---|---|
| 0 | 36 | 0.25 | 0 | 3 | | 1478.6 |
| 1 | 36 | 0.15 | 15 | 3 | | 1479.3 |
| 2 | 27 | 0.2 | 45 | 2.5 | | 1479.9 |
| 3 | 25 | 0.4 | 85 | 2.5 | | 1480.2 |
| 4 | 17.2 | 0.55 | 105 | 2.5 | | 1480.3 |
| 5 | 14.8 | 0.65 | 130 | 2.5 | | 1479.8 |
| 6 | 14 | 0.65 | 155 | 2.5 | | 1490.6 |
| 7 | 14 | 0.65 | 160 | 2.5 | | 1490.8 |

TABLE 2

SHOWING THE TEST CONDITIONS USED

| Volumetric flow rate l/min | Linear flow rate cm/hr | Flow direction |
|---|---|---|
| 3 | 150 | Down |
| 2 | 100 | Down |
| 1 | 50 | Down |
| 1 | 50 | Up |
| 2 | 100 | Up |
| 3 | 150 | Up |
| 318 hour stability run | 150 | Down |
| 3 | 150 | Down |
| 2 | 100 | Down |
| 1 | 50 | Down |
| 1 | 50 | Up |
| 2 | 100 | Up |
| 3 | 150 | Up |

TABLE 3

| Pack Number | Results | Before Stability: Downflow | Before Stability: Upflow | After Stability: Downflow | After Stability: Upflow | Mean | Packing Differences to B2 and B3 |
|---|---|---|---|---|---|---|---|
| B1 | Pl/m | 3384 | n/a | 3100 | n/a | 3242 | Packed in PO$_4$ buffer at 1.3 bar |
| | Asymmetry | 1.5 | n/a | 1.25 | n/a | 1.375 | |
| B2 | Pl/m | 4881 | 3842 | 3857 | 3770 | 4088 | — |
| | Asymmetry | 1.4 | 1.4 | 1.4 | 1.3 | 1.4 | |
| B3 | Pl/m | 4308 | 4328 | 4267 | 4147 | 4263 | — |
| | Asymmetry | 1.4 | 1.4 | 1.5 | 1.6 | 1.5 | |
| B4 | Pl/m | 3485 | 3449 | 3142 | 3112 | 3297 | 5 minutes to pack 1.4 bar. Before |
| | Asymmetry | 1.4 | 1.4 | 1.6 | 1.8 | 1.6 | |

TABLE 3-continued

| Pack Number | Results | Before Stability: Downflow | Before Stability: Upflow | After Stability: Downflow | After Stability: Upflow | Mean | Packing Differences to B2 and B3 |
|---|---|---|---|---|---|---|---|
| B5 | Pl/m | 2443 | 2161 | 2597 | 2398 | 2400 | stability downflow at 50 cm/hr Took 7 minutes (stopped & started) to pack at 2.2 bar |
|  | Asymmetry | 1.1 | 1.8 | 1.5 | 1.4 | 1.5 | |

TABLE 4

Comparing the Pack Profiles as Observations from Graph

| Pack Number | Plates/metre (2 sig. Fig.) | Initial Third of Pack Phase 1 | Middle Third of Pack Phase 2 | Final Third of Pack Phase 3 |
|---|---|---|---|---|
|  |  | Packing Rate mm/min | | |
| 1 | 3200 | 33 | 40 | 60 |
| 2 | 4100 | 26 | 82 | 65 |
| 3 | 4200 | 27 | 77 | 77 |
| 4 | 3300 | 41 | 50 | 26 |
| 5 | 2400 | 24 | 11 | 39 |

The invention claimed is:

1. Chromatography apparatus comprising a chromatography column having a housing wall with side wall and end wall portions defining an internal bed space for containing a particulate chromatography medium, the apparatus comprising at least one ultrasound transmitter on the outside of the housing side wall, disposed to transmit an ultrasound signal through the housing wall and the bed space, and a detector to detect the transmitted signal.

2. Chromatography apparatus according to claim 1, in which at least one said ultrasound transmitter is comprised in a transceiver unit also comprising a said detector.

3. Chromatography apparatus according to claim 1, in which plural said transmitters and/or plural said detectors therefor are distributed along the column side wall in a direction between an inlet and an outlet of the column.

4. Chromatography apparatus according to claim 1, in which the column is a vertical cylinder.

5. Chromatography apparatus according to claim 4, in which the column has a steel side wall.

6. Chromatography apparatus according to claim 1, comprising a control processor operatively connected to the ultrasound transmitter and detector and programmed to determine a speed and/or attenuation for the transmissions between them via the internal bed space.

7. Chromatography apparatus according to claim 1, in which the chromatography column has a port through its housing wall adapted for the injection of a slurry of particulate medium for packing the column.

8. Chromatography apparatus according to claim 7, in which plural said transmitters and/or plural said detectors are distributed along the column to enable detection of ultrasound transmissions along a corresponding plurality of paths through the internal bed space.

9. Chromatography apparatus according to claim 8, in which a control processor is operatively connected to the transmitters and detectors and programmed to determine, for said plurality of transmission paths, respective transmission speeds and/or attenuations.

10. Chromatography apparatus comprising a chromatography column having a column housing defining a bed space to contain in use a bed of particulate chromatography medium, through which in use a process liquid containing components to be separated is passed to separate the components chromatographically, and characterized by detection means for detecting in the bed space the passage of a band of a said component in the packed bed, said detection means comprising means for transmitting ultrasound signals through the bed space and for detecting the signals after they have transmitted through the bed space along a transmission path, whereby the time of flight or speed and/or attenuation of the signals transmitting through the packed bed in use is affected by whether a said component is present in the bed on the transmission path, the apparatus also comprising a visual display outside the column connected to said detection means to indicate the output thereof.

11. Chromatography apparatus according to claim 10, which the chromatography column is a vertical cylinder.

12. Chromatography apparatus according to claim 10, in which the chromatography column side wall is opaque.

13. Chromatography apparatus comprising a chromatography column having a housing wall with side wall and end wall portions defining an internal bed space, characterized by plural ultrasound transmitters distributed along the housing side wall, disposed to transmit ultrasound signals across the column through the bed space, a detector to detect the signals thus transmitted, said transmitter and/or detector being on the outside of the housing side wall, so that the ultrasound signals are transmitted to the detector through the wall as well as through the bed space.

14. Chromatography apparatus according to claim 13, in which at least one said ultrasound transmitter is comprised in a transceiver unit also comprising a said detector.

15. Chromatography apparatus according to claim 13, in which the chromatography column is a vertical cylinder.

16. Chromatography apparatus according to claim 13, in which the chromatography column side wall is opaque.

17. Chromatography apparatus according to claim 10, in which plural ultrasound transmitters and plural ultrasound detectors are combined in a plurality of respective ultrasound transceivers distributed axially along the column side wall.

* * * * *